US012458547B2

(12) United States Patent
Johnson et al.

(10) Patent No.: US 12,458,547 B2
(45) Date of Patent: Nov. 4, 2025

(54) ABSORBENT PADS FOR WOUND DRESSINGS

(71) Applicant: MEDTRADE PRODUCTS LIMITED, Crewe (GB)

(72) Inventors: Neil Johnson, Northwich (GB); Jennifer Haynes, Crewe (GB)

(73) Assignee: MEDTRADE PRODUCTS LIMITED, Crewe (GB)

(*) Notice: Subject to any disclaimer, the term of this patent is extended or adjusted under 35 U.S.C. 154(b) by 486 days.

(21) Appl. No.: 17/782,628

(22) PCT Filed: Dec. 4, 2020

(86) PCT No.: PCT/GB2020/053132
§ 371 (c)(1),
(2) Date: Jun. 3, 2022

(87) PCT Pub. No.: WO2021/111151
PCT Pub. Date: Jun. 10, 2021

(65) Prior Publication Data

US 2023/0012868 A1 Jan. 19, 2023

(30) Foreign Application Priority Data

Dec. 4, 2019 (GB) ..................................... 1917732

(51) Int. Cl.
*A61F 13/512* (2006.01)
*A61F 13/45* (2006.01)

(52) U.S. Cl.
CPC .......... *A61F 13/5126* (2013.01); *A61F 13/45* (2013.01)

(58) Field of Classification Search
CPC ................ A61F 13/01038; A61F 13/00; A61F 13/01021; A61F 13/0233; A61F 13/0243;
(Continued)

(56) References Cited

U.S. PATENT DOCUMENTS

2004/0126413 A1 7/2004 Sigurjonsson
2013/0084323 A1 4/2013 Riebman et al.
(Continued)

FOREIGN PATENT DOCUMENTS

AU 2009200105 B2 4/2015
CN 107518983 A 12/2017
(Continued)

OTHER PUBLICATIONS

International Search Report dated Mar. 5, 2021 for corresponding International Application No. PCT/GB2020/053132.

*Primary Examiner* — Ophelia A Hawthorne
(74) *Attorney, Agent, or Firm* — Tarolli, Sundheim, Covell & Tummino LLP

(57) ABSTRACT

The present invention concerns extensible absorbent pads for wound dressings. The absorbent pad has a plurality of fenestrations therein, wherein the fenestrations are arranged in a pattern about a central point. The pattern comprises one or more fenestrations having symmetry about a cardinal axis and one or more fenestrations having symmetry about an intercardinal axis, wherein the cardinal and intercardinal axes cross at the central point. The absorbent pads of the present invention can be used in advanced wound care dressing applications where additional stretch and extensibility of the dressing will assist clinicians in applying the dressing to difficult to dress anatomical areas.

28 Claims, 8 Drawing Sheets

(58) Field of Classification Search

CPC .............. A61F 13/0263; A61F 13/0266; A61F 13/061; A61F 13/10; A61F 2013/00595; A61F 2013/00604; A61F 13/0213; A61F 13/02; A61F 13/0209; A61F 13/5126; A61F 13/45; A61F 13/0203; A61F 13/15203

See application file for complete search history.

(56) References Cited

U.S. PATENT DOCUMENTS

| | | | | |
|---|---|---|---|---|
| 2018/0289555 | A1 | 10/2018 | Gogolowski | |
| 2020/0306093 | A1* | 10/2020 | Rivest | A61F 13/02 |

FOREIGN PATENT DOCUMENTS

| | | | |
|---|---|---|---|
| EP | 0875222 | A1 | 11/1998 |
| GB | 815121 | A | 6/1959 |
| WO | 2016030047 | A | 3/2016 |
| WO | 2018041805 | A1 | 3/2018 |
| WO | 2019027731 | A1 | 2/2019 |
| WO | 2019027806 | A1 | 2/2019 |
| WO | 2020226511 | A1 | 12/2020 |

* cited by examiner

ABSORBENT PADS FOR WOUND DRESSINGS

RELATED APPLICATIONS

The present application is a U.S. National Stage application under 35 USC 371 of PCT Application Serial No. PCT/GB2020/053132, filed on 4 Dec. 2020; which claims priority from GB Patent Application No. 1917732.8, filed 4 Dec. 2019; and from GB Patent Application No. 1917732.8, filed 4 Dec. 2019, the entirety of each of which are incorporated herein by reference.

TECHNICAL FIELD OF THE INVENTION

The present invention relates to absorbent pads. In particular, but not exclusively, the invention concerns extensible absorbent pads for wound dressings.

BACKGROUND TO THE INVENTION

Absorbent pads are used extensively within the advanced wound care domain. Such pads often form the core of wound dressings as they are able to absorb a large amount of exudate from a wound over a period of days; either locking the exudate away within their structure or wicking it to other parts of the dressing for transpiration to the surrounding environment. An example of an absorbent pad includes Optifoam Gentle SA by Medline Industries.

The absorbent pads may have a laminate structure. The absorbent laminate components are typically the most rigid and least extensible parts of the construction, often acting as the rate limiting factor in the extensibility of the overall dressing. This lack of stretch and conformability can be burdensome for clinicians, especially when applying wound dressings having such absorbent pads to difficult to dress anatomical areas such as knees, hips, elbows, feet and amputation sites. Once applied, the rigid wound dressings can also prematurely detach from the wound or skin surface before full saturation capacity has been reached as they cannot respond and conform to the patient's bodily movements. This can result in clinician dissatisfaction, with an increased number of dressing changes placing a higher burden on time. Additional unnecessary wound dressing changes also significantly increase healthcare authority costs, both via purchasing of the wound dressings and disposal of clinical waste.

Advanced wound care dressing manufacturers have sought to address this clinical issue via multiple design solutions. Several wound dressings, in particular dressings designed for post-operative wounds, feature absorbent pads with cut fenestration patterns. Such dressings can feature a repeat fenestration pattern or fenestrations orientated along a single axis of the dressing, such as in Optifoam Gentle SA of Medline Industries. Whilst such dressings impart additional extensibility, there is a need to increase the extensibility of the wound dressings for use on difficult to dress anatomical areas.

Embodiments of the present invention seek to overcome these or other disadvantages and/or to provide an improved absorbent pad.

SUMMARY OF THE INVENTION

According to the present invention, there is provided an absorbent pad for a wound dressing, the pad having a plurality of fenestrations therein, wherein the fenestrations are arranged in a pattern about a central point, wherein the pattern comprises one or more fenestrations having symmetry about a cardinal axis and one or more fenestrations having symmetry about an intercardinal axis, the cardinal and intercardinal axes crossing at the central point.

Providing a pattern of fenestrations, wherein one or more fenestrations has symmetry about a cardinal axis and one or more fenestrations has symmetry about an intercardinal axis, can achieve certain advantages in providing extensibility in more than one direction to a wound dressing incorporating an absorbent pad having such a fenestration pattern. Beneficially, this enables the pad to conform to more difficult to dress anatomical areas of the body of a patient.

The absorbent pad of the present invention can be used in advanced wound care dressing applications where additional stretch and extensibility of the dressing will assist clinicians in applying the dressing to difficult to dress anatomical areas. The additional extensibility will also yield anthropometric benefits, permitting an additional range of motion for patients resulting from a dressing that conforms and stretches to mirror patient movements. Moreover, wound dressings comprising an absorbent pad of the present invention will remain in place for longer, thus reducing the burden on clinicians' time via a reduced number of dressing changes. This yields economic savings and provides a lower environmental burden through a reduction in disposable clinical waste.

The term 'cardinal axes' is used herein to refer to two perpendicular axes that intersect at the central point. The term 'cardinal axis' is used herein to refer to one of the cardinal axes.

The term 'intercardinal axes' is used herein to refer to two perpendicular axes that intersect at the central point, wherein each axis bisects the opposite angles between the cardinal axes. The term 'intercardinal axis' is used herein to refer to one of the intercardinal axes.

The term 'secondary intercardinal axes' is used herein to refer to four axes that intersect at the central point at 45° to each other, wherein each axis bisects the opposite angles between a cardinal axis and an intercardinal axis. The term 'secondary intercardinal axis' is used herein to refer to one of the secondary intercardinal axes.

The term 'secondary intercardinal regions' is used herein to refer to the eight segments located between the cardinal axes and the intercardinal axes. The term 'secondary intercardinal region' is used herein to refer to one of the secondary intercardinal regions.

The pattern may comprise from 2 to 100 fenestrations per 0.01 $m^2$ of absorbent pad. The pattern may comprise from 10 to 70 fenestrations per 0.01 $m^2$ of absorbent pad. The pattern may comprise from 20 to 60 fenestrations per 0.01 $m^2$ of absorbent pad. The pattern may comprise from 25 to 50 fenestrations per 0.01 $m^2$ of absorbent pad. The pattern may comprise from 30 to 40 fenestrations per 0.01 $m^2$ of absorbent pad.

The pattern may comprise one or more fenestrations having symmetry about one cardinal axis and one or more fenestrations having symmetry about the other cardinal axis. The pattern may comprise a plurality of fenestrations having symmetry about one cardinal axis and a plurality of fenestrations having symmetry about the other cardinal axis.

The pattern may comprise a plurality of fenestrations having symmetry about one or both cardinal axes. The pattern may comprise from one to ten fenestrations having symmetry about one or both cardinal axes. The pattern may comprise from four to eight fenestrations having symmetry about one or both cardinal axes. The pattern may comprise from six to eight fenestrations having symmetry about one or both cardinal axes. The pattern may comprise two, three, four, five, six, seven, eight, nine or ten fenestrations having symmetry about one or both cardinal axes.

One or more of the fenestrations may be located on a cardinal axis, where such one or more fenestrations have symmetry about that cardinal axis.

The pattern may comprise one or more fenestrations having symmetry about one intercardinal axis and one or more fenestrations having symmetry about the other intercardinal axis. The pattern may comprise a plurality of fenestrations having symmetry about one intercardinal axis and a plurality of fenestrations having symmetry about the other intercardinal axis.

The pattern may comprise a plurality of fenestrations having symmetry about one or both intercardinal axes. The pattern may comprise from one to ten fenestrations having symmetry about one or both intercardinal axes. The pattern may comprise from four to eight fenestrations having symmetry about one or both intercardinal axis. The pattern may comprise from six to eight fenestrations having symmetry about one or both intercardinal axes. The pattern may comprise two, three, four, five, six, seven, eight, nine or ten fenestrations having symmetry about one or both intercardinal axis.

One or more of the fenestrations may be located on an intercardinal axis, where such one or more fenestrations have symmetry about that intercardinal axis.

Providing a pattern comprising a plurality of fenestrations having symmetry about the cardinal and/or intercardinal axes improves the extensibility in more than one direction of a pad incorporating the pattern. The absorbent pad of the present invention can show improved extensibility in all directions.

The pattern may further comprise one or more fenestrations having symmetry about one or more of the secondary intercardinal axes.

The pattern may comprise one or more fenestrations having symmetry about one, two, three or four of the secondary intercardinal axes.

The pattern may comprise a plurality of fenestrations having symmetry about one or more of the secondary intercardinal axes. The pattern may comprise from one to ten fenestrations having symmetry about the one or more secondary intercardinal axes. The pattern may comprise from four to eight fenestrations having symmetry about the one or more secondary intercardinal axes. The pattern may comprise from six to eight fenestrations having symmetry about the one or more secondary intercardinal axes. The pattern may comprise two, three, four, five, six, seven, eight, nine or ten fenestrations having symmetry about the one or more secondary intercardinal axes.

One or more of the fenestrations may be located on a secondary intercardinal axis, where such one or more fenestrations have symmetry about that secondary intercardinal axis.

The pattern may comprise a fenestration located in a secondary intercardinal region that does not have symmetry about the secondary intercardinal axis passing through that secondary intercardinal region. The pattern may comprise a plurality of fenestrations located in one or more of the secondary intercardinal regions that do not have symmetry about the secondary intercardinal axis passing through that secondary intercardinal region. Such one or more fenestrations in a secondary intercardinal region may have symmetry with one or more fenestrations in another secondary intercardinal region about a cardinal, intercardinal and/or secondary intercardinal axis.

Providing a pattern comprising a plurality of fenestrations having symmetry about the one or more secondary intercardinal axes, and/or comprising one or more fenestrations in one or more of the secondary intercardinal regions, improves the multi-directional extensibility of an absorbent pad incorporating such a pattern. The absorbent pad can show improved extensibility in all directions.

The pattern of fenestrations may radiate outwardly from the central point. Beneficially, a radiating pattern of fenestrations has been found to provide improved extensibility of the absorbent pad in any direction.

Each cardinal, intercardinal and secondary intercardinal axis extends in opposing directions from the central point.

The fenestrations may radiate outwardly from the central point along the cardinal and intercardinal axes.

The fenestrations may radiate outwardly from the central point along the cardinal and intercardinal axes, with additional fenestrations being located in one or more secondary intercardinal regions.

The number of fenestrations located on a cardinal, intercardinal and/or secondary intercardinal axis in one direction from the central point may be equal to the number of fenestrations located on the same cardinal, intercardinal and/or secondary intercardinal axis in the opposite direction.

Beneficially, it has been found that having an equal number of fenestrations in opposing directions from the central point along a cardinal, intercardinal and/or secondary intercardinal axis, improves the extensibility of the absorbent pad. For example, the absorbent pad may comprise the same number of fenestrations in opposing directions along one or both cardinal axes. Similarly, the absorbent pad may comprise the same number of fenestrations in opposing directions along one or both intercardinal axes. Finally, the absorbent pad may comprise the same number of fenestrations in opposing directions along one, two, three or four secondary intercardinal axes.

It has also been found that the orientation of the fenestrations in opposing directions can improve the extensibility of the absorbent pad or wound dressing. The fenestrations located in opposing directions along a cardinal, intercardinal or secondary intercardinal axis may be symmetrical about the axis perpendicular to that cardinal, intercardinal or secondary intercardinal axis.

Preferably, the pattern of fenestrations is radiating outwardly from the central point. In one embodiment, the pattern comprises opposing fenestrations in the directions of each of the cardinal, intercardinal and secondary intercardinal axes. Such embodiments have resulted in improved multi-directional extensibility.

In a preferred embodiment, the pattern of fenestrations in the absorbent pad may be symmetrical about at least one of the cardinal, intercardinal or secondary intercardinal axes. Preferably still, the pattern of fenestrations in the absorbent pad may be symmetrical about both the cardinal axes and the intercardinal axes.

A fenestration may comprise a slit in the absorbent pad.

The slit may vary in length. The length of the slit may be proportional to the dimensions of the wound dressing.

The fenestrations may vary in geometrical shape.

All of the fenestrations may be the same geometrical shape. Alternatively, the fenestrations may be present in two or more different geometrical shapes.

All of the fenestrations may be the same size. Alternatively, the fenestrations may be present in two or more different sizes.

One or more fenestrations may have an arc shape. The arc may have any suitable arc length. The arc shape is preferably a semi-circular arc.

For pads comprising a plurality of arc-shaped fenestrations, all fenestrations may have the same arc length. Alternatively, the fenestrations may have a variety of arc lengths. The arc lengths may range from 4 mm to 12 mm in diameter. Preferable, the arc length is 8 mm in diameter.

The arcs may face toward the central point. In such embodiments, the apex of the arc faces towards the central point. Alternatively, the arcs may face away from the central point. In such embodiments, the apex of the arc faces away from the central point. The plurality of fenestrations may comprise a mixture of arcs facing towards the central point and arcs facing away from the central point.

For example, one or more arc shaped fenestrations symmetrical about a cardinal axis may face toward the central point and one or more arc shaped fenestrations symmetrical about an intercardinal axis may face away from the central point. Alternatively, one or more arc shaped fenestrations symmetrical about a cardinal axis may face away from the central point and one or more arc shaped fenestrations symmetrical about an intercardinal axis may face toward the central point.

One or more fenestrations may have a cross shape. The cross may comprise two intersecting slits. The two intersecting slits may intersect at the midpoint of each slit. The two pairs of opposite angles created by the intersecting slits may add to 180°.

For pads comprising a plurality of cross-shaped fenestrations, the intersecting slits of all fenestrations may have the same length. Alternatively, the intersecting slits of all fenestrations may have a variety of slit lengths. For example, the pattern of fenestrations may comprise cross-shaped fenestrations of two different sizes.

The plurality of fenestrations may comprise a mixture of cross shape fenestrations and arc shape fenestrations.

The absorbent pad may comprise a fenestration located at or near to the central point. Incorporating a central fenestration into the pattern on the absorbent pad has been found to improve extensibility compared to patterns not comprising a central fenestration. Preferably, the central fenestration is located at the central point. The plurality of fenestrations as described herein may radiate outwardly from the central fenestration.

The central fenestration may comprise any size and/or geometrical shape. The central fenestration may be different in size to the other fenestrations in the pattern.

The central fenestration may be different in geometrical shape to the other fenestrations in the pattern.

The central fenestration may be larger in size than the fenestrations arranged about the central point. Preferably, the central fenestration is larger than the fenestrations radiating outwardly from the central point.

The central fenestration can be the same shape as the fenestrations arranged about the central point. For example, the central fenestration can be the same shape as the fenestrations radiating outwardly from the central point. Alternatively, the central fenestration can be a different shape to the fenestrations arranged about the central point. For example, the central fenestrations can be a different shape to the fenestrations radiating outwardly from the central point.

The geometrical shape of the central fenestration may be formed by one or more slits in the pad. For example, the central fenestration may comprise a single slit. The single slit may be linear or non-linear. Alternatively, the central fenestration may comprise two slits. The two slits may intersect each other at a point along their length. The two slits may alternatively abut each other along their length.

The central fenestration may have rotational symmetry. The rotational symmetry may be about the central point. The central fenestration may have n-fold rotational symmetry, wherein n is an integer from two to ten. The central fenestration may have two, three, four, five, six, seven, eight, nine or ten-fold rotational symmetry. For example, where the central fenestration comprises a single slit, it will have two-fold rotational symmetry about the central point located on its length.

The central fenestration may have a cross shape.

The cross may comprise two intersecting slits. In such an embodiment, the central fenestration may have two or four-fold rotational symmetry. The intersecting slits may intersect at the midpoint of each slit. The two slits may bisect each other at the central point. The intersecting slits may be aligned with the cardinal axes. Alternatively, the intersecting slits may be aligned with the intercardinal axes. Alternatively still, the intersecting slits may be aligned with two of the secondary intercardinal axes. In such embodiments, the two pairs of opposite angles created by the intersecting slits add to 180°. In alternative embodiments, one of the pairs of opposite angles created by the intersecting slits may add to greater than 180°.

The central fenestration may comprise a cross shape that is proportional in size to the dimensions of the wound dressing. The length of the slits forming the cross may be extended in length for larger wound dressings or reduced in length for smaller wound dressings. For example, in a wound dressing measuring 0.1 m×0.1 m, the slits that form a central cross shape may be from 0.015 m to 0.02 m in length.

In alternative embodiments, the central fenestration may comprise two opposing arcs. The opposing arcs may be semi-circular arcs. The two arcs may abut each other at the apex of each arc. The two arcs may abut each other at the central point.

In one embodiment, the central fenestration may comprise a triskelion shape. In such an embodiment, the central fenestration may comprise three slits extending outwardly from the central point, such that the fenestration has three-fold rotational symmetry about the central point. The slits may be liner or curved.

In an alternative embodiment, the central fenestration may comprise a tetraskelion shape. In such an embodiment, the central fenestration may comprise four slits extending outwardly from a central point, such that the fenestration has four-fold rotational symmetry about the central point. The slits may be linear or curved.

Good extensibility results have been observed with a pattern comprising a cross-shaped central fenestration, with the one or more fenestrations having symmetry about the cardinal and intercardinal axes being arc shaped. In such an embodiment, the arc shaped fenestrations may radiate outwardly from the central fenestration. The arc shaped fenestrations preferably face toward the central point. Preferably, the pattern comprises a plurality of arc shaped fenestrations located on the cardinal and intercardinal axes, each fenestration having symmetry about the axis on which it is located.

The absorbent pad may be a single layer. Alternatively, the absorbent pad may have a laminate structure.

The absorbent pad may comprise or consist of an absorbent material. The absorbent material may be a superabsorbent material. The fenestrations may partially penetrate the absorbent material or penetrate through the absorbent material.

The laminate structure may comprise a plurality of layers. The laminate may comprise two, three, four, five, six, seven, eight, nine, ten or more layers. Preferably, the laminate comprises three layers.

The layers may be bonded together using an adhesive between the layers. The adhesive may be a thermal adhesive. The adhesive may comprise any suitable thermal adhesive known in the art. For example, the thermal adhesive may be a thermoplastic adhesive, such as polycaprolactone.

One or more of the layers may comprise or consist of an absorbent material. The absorbent material may be a superabsorbent material.

One or more of the layers may comprise or consist of a polymeric foam. Preferably, the polymeric foam is polyurethane foam.

The layer of absorbent material may itself comprise a laminate structure. The absorbent material may comprise a plurality of layers. The plurality of layers may comprise one or more absorbent materials. The absorbent materials may comprise a superabsorbent material and fluff pulp. The plurality of layers may comprise separate layers of superabsorbent material and fluff pulp. The separate layers may alternate between superabsorbent material and fluff pulp. Alternatively, the layers may comprise a mixture of superabsorbent material and fluff pulp.

The absorbent material may comprise carboxymethyl cellulose, alginate, chitosan salt, polyurethane, or a combination of any one or more of the aforesaid.

The term 'absorbent material' is used herein to refer to a physiologically acceptable material that is capable of absorbing fluid, such as wound exudate.

In one embodiment, the absorbent pad may consist essentially of an absorbent material.

The term 'superabsorbent material' is used herein to refer to a hydrophilic material that is water-swellable, but not water soluble, and which is capable of absorbing fluid to greater than 2000% with a fluid retention of greater than 85%. Preferably, the superabsorbent material is capable of absorbing fluid to greater than 2500% with a fluid retention of greater than 90%.

The term 'water-swellable' is used herein to refer to a material that, when contacted with water or water-containing fluid, will absorb the fluid and swell, but will not substantially dissolve in that fluid.

The term 'water soluble' is used herein to refer to a material that, when contacted with water or a water-containing fluid, will dissolve in that fluid.

The superabsorbent material may be selected from polymeric materials such as poly(vinyl) alcohol (PVA), poly (ethylene oxide) (PEO) and poly(acrylic acid).

The superabsorbent material may be chemically modified. For example, the superabsorbent material may be a polymeric material obtained by graft polymerisation of acrylic acid onto a chain of carboxymethyl cellulose.

The superabsorbent material may comprise a chemically modified material selected from starch, cellulose and polymeric materials such as poly(vinyl alcohol) (PVA), poly (ethylene oxide) (PEO), and poly(acrylic acid). The poly (acrylic acid) may be a partially neutralised, lightly cross-linked poly(acrylic acid).

The terms 'cross-linking' and 'cross-linked' are used herein to refer to two or more polymer chains being linked by a primary bond, such as a covalent bond.

The term 'lightly cross-linked' is used herein to refer to embodiments wherein the number of cross-linking primary bonds in the superabsorbent material is less than the total number of possible cross-linking bonds.

In some embodiments, the superabsorbent material is selected from polymeric materials such as PVA, PEO, and poly(acrylic acid), preferably a partially neutralised, lightly cross-linked poly(acrylic acid).

Typically, the superabsorbent material is a partially neutralised, lightly crosslinked poly(acrylic acid).

One or more of the layers may be a wicking layer. The term 'wicking layer' is used herein to refer to a layer of the laminate that primarily directs wound exudate in multiple directions in the X-Y plane of the layer. The X-Y plane of the layer is defined by the length and width of the layer.

The wicking layer may comprise a biologically acceptable polymer material that has a wicking rate the same or equal to that of the absorption layer. Suitable biologically acceptable polymer materials may be selected from the group consisting of polyurethane, polyvinyl chloride, Styrofoam, polyimide and silicone.

Preferably, the biologically acceptable polymer is polyurethane.

The wicking layer may be in the form of a textile, a film or a foam. Preferably, the wicking layer is in the form of a foam, preferably still an open celled foam. Thus, the biologically acceptable polymer materials may be selected from the group consisting of polyurethane foam, polyvinyl chloride foam, Styrofoam, polyimide foam and silicone foam.

Good results have been observed wherein the wicking layer comprises polyurethane foam. The polyurethane foam may be open-celled so as to allow for the passage of wound exudate through the foam and into the adjacent layer. Closed celled foams are not preferred for the wicking layer as they do not readily allow the passage of exudate through the foam.

The layers of the absorption pad may be bonded using heat bonding or at least one adhesive. Preferably, the layers are bonded using an adhesive.

The adhesive may be applied to either or both of the surfaces that will be contacted with each other. The adhesive may be applied across substantially all of either or both surfaces or, alternatively, across a portion or portions thereof.

The adhesive may be in the form of a powder, a liquid, a web or a net. The web may be an acrylic web.

The adhesive may comprise a meltable adhesive and/or a pressure sensitive adhesive, or the like. The meltable adhesive may be a heat-bonding adhesive. The pressure sensitive adhesive may be acrylic based.

The adhesive may be in the form of a layer between the layers of the laminate. Preferably, the layer of adhesive is porous so as to allow transmission of the wound exudate.

The adhesive may be a powder adhesive. The powder may be scattered onto one or more surfaces of the layers to be bonded and then passed through a heat tunnel.

The fenestrations may penetrate through the entire thickness of the pad. Alternatively, the fenestrations may penetrate partially through the thickness of the pad. Preferably, the fenestrations penetrate through the entire thickness of the pad as this has been found to provide a pad having a greater extensibility. Beneficially, this enables greater conformity to difficult to dress anatomical areas of the body of a patient.

The absorbent pad may comprise two or more patterns of fenestrations, each pattern arranged about a different central point. The two or more patterns may be the same or different. The two or more patterns may comprise any of the features disclosed herein as desired or as appropriate.

According to the present invention, there is provided an absorbent pad for a wound dressing, the pad having a plurality of fenestrations therein, wherein the fenestrations are present in two or more different geometrical shapes. The absorbent pad and fenestrations may incorporate any of the features described herein as desired or as appropriate.

The absorbent pad may be incorporated into a wound dressing.

According to a further aspect of the present invention, there is provided a wound dressing comprising an absorbent pad as disclosed herein.

The wound dressing may be in the form of an island dressing. Typically, island dressings comprise a backing layer having an absorbent pad located on a wound facing surface thereof. The backing layer comprises a border portion that extends beyond the edges of the absorbent pad, with an adhesive located on the wound facing surface of the border portion for adhering the dressing to the wound-surrounding skin of a patient.

The backing layer may comprise a water vapour permeable, waterproof film. The backing layer may comprise or consist of polyurethane. Typically, the backing layer is fully or partially coated with an adhesive to adhere it to the absorbent pad. The adhesive may be any suitable adhesive known in the art. Preferably, the adhesive is an acrylic adhesive. Preferably, the adhesive is pattern coated.

The adhesive may comprise any suitable skin-contact adhesive known in the art. Preferably, the adhesive is a silicone adhesive, such as a polydimethylsiloxane adhesive. Alternatively, the adhesive can be an acrylic adhesive, a polyurethane adhesive, a hydrogel adhesive, or any combinations thereof.

The backing layer may have a thickness of from 5-50 microns, preferably 10-30 microns.

The wound dressing may further comprise a removable protecting layer. The removable protecting layer may be a peelable protecting layer. The removable protecting layer may cover the wound facing surface of the absorbent pad and the wound facing surface of the border portion of the backing layer. The protecting layer facilitates storage of the wound dressing without detriment to the absorbent pad or the skin-contact adhesive on the backing layer. The protecting layer is intended for removal prior to application of the dressing to a wound.

The removable protecting layer may comprise two parts that are separately removable via one or more tabs.

According to a further aspect of the present invention, there is provided a method of manufacturing an article, said method comprising applying a plurality of fenestrations to an absorbent pad, wherein the fenestrations are arranged in a pattern about a central point, wherein the pattern comprises one or more fenestrations having symmetry about a cardinal axis and one or more fenestrations having symmetry about an intercardinal axis, the cardinal and intercardinal axes crossing at the central point.

The method may comprise the step of forming an absorbent pad by bonding a polymeric foam to an absorbent material to form a laminate structure. The polymeric foam may be a polyurethane foam.

The polymeric foam may be bonded to the absorbent material with a thermal bonding agent through a lamination process. The lamination process may comprise the application of heat and pressure.

Alternatively, the polymeric foam may be bonded to the absorbent material using a pressure sensitive adhesive.

The laminate structure may be cut to the desired dimensions of the absorbent pad. The fenestrations may be applied to the absorbent pad at the same time as the laminate structure is being cut to the desired dimensions.

According to a further aspect of the present invention, there is provided a method of manufacturing a wound dressing, said method comprising the steps of adhering an absorbent pad as described herein to a backing layer as described herein.

The absorbent pad may be adhered to the backing layer using an adhesive as described herein.

The method of manufacturing a wound dressing may comprise the further step of applying to a wound facing surface of the absorbent pad a removable protecting layer as described herein.

The wound dressing may be cut and shaped as desired or as appropriate.

According to a further aspect of the present invention, there is provided a method of absorbing fluid discharged from a physiological target site of a human or animal body, or of stemming a flow of a fluid discharged from a physiological target site of a human or animal body, comprising applying to the physiological target site an absorbent pad as defined herein or a wound dressing as defined herein.

According to a further aspect of the present invention, there is provided a use of an absorbent pad as defined herein, or a wound dressing as defined herein, in absorbing fluid discharged from a physiological target, or in stemming a flow of a fluid discharged from a physiological target site.

According to a further aspect of the present invention, there is provided an absorbent pad as defined herein, or a wound dressing as defined herein, for use in absorbing fluid discharged from a physiological target, or for use in stemming a flow of a fluid discharged from a physiological target site.

The further aspects of the present invention may incorporate any of the features of the other aspects of the invention described herein as desired or as appropriate.

DETAILED DESCRIPTION OF THE INVENTION

In order that the invention may be more clearly understood one or more embodiments thereof will now be described, by way of example only, with reference to the accompanying drawings, of which:

Figure 1:
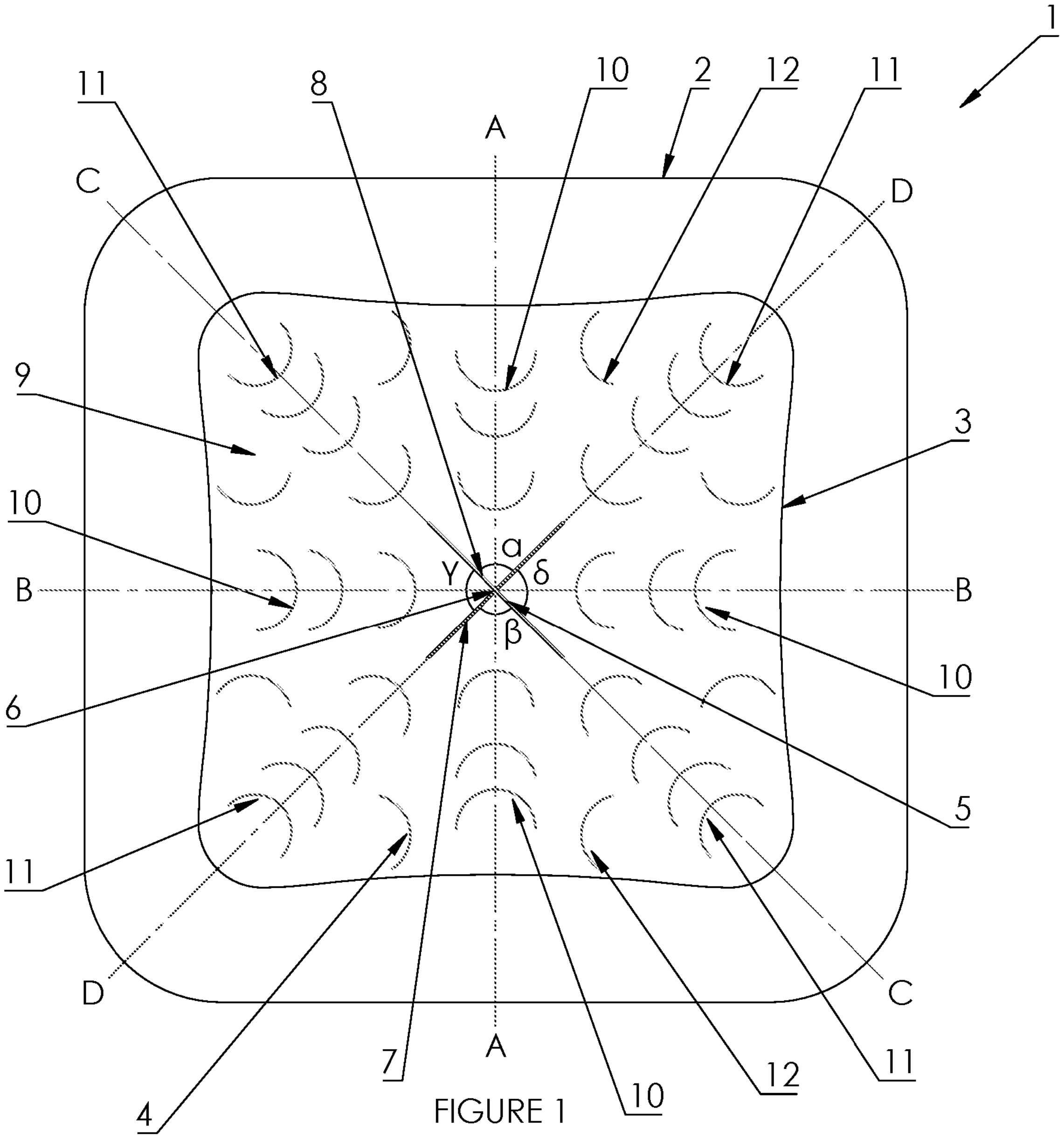
FIG. 1 is a plan view of a first embodiment of a wound dressing comprising an absorbent pad.
Figure 2:
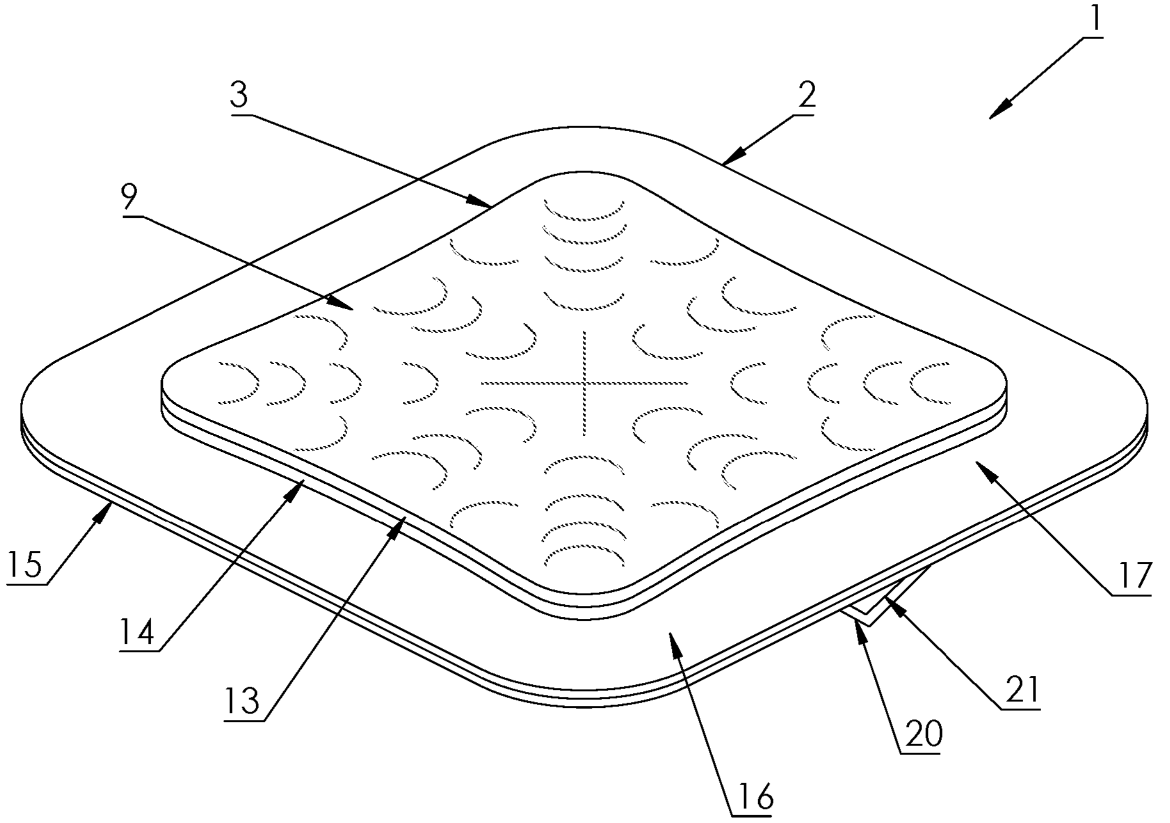
FIG. 2 is a perspective view of the embodiment of FIG. 1.
Figure 3:
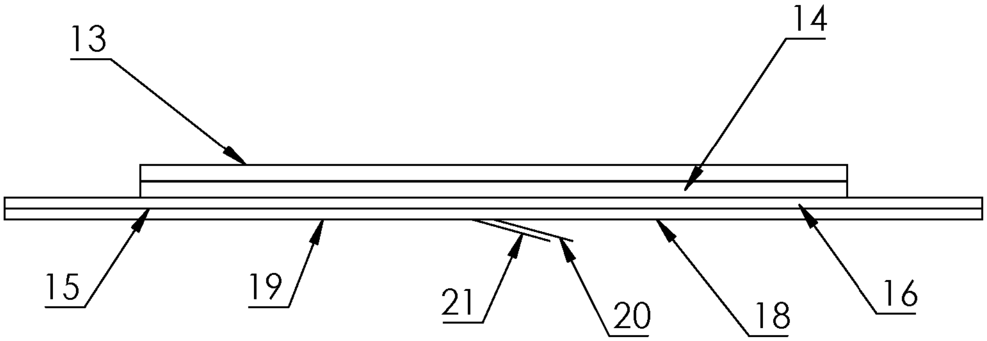
FIG. 3 is a side view of the embodiment of FIG. 1.

Referring to FIGS. 1-3, there is shown a wound dressing 1 comprising a backing layer 2 and an absorbent pad 3. The absorbent pad 3 comprises a plurality of fenestrations 4. Each of the fenestrations 4 has an arc shape. The majority of the fenestrations 4 have a semi-circular arc shape. The fenestrations 4 all face towards a central fenestration 5 which is located at a central point 6.

The central fenestration 5 has a cross-shape, having two intersecting slits 7, 8. The intersecting slits 7, 8 create two pairs of opposite angles α, β and γ, δ. Each pair of opposite angles adds to 180°.

The absorbent pad 3 is in the shape of a rounded-edge square and has a wound facing surface 9 into which the fenestrations 4 are cut. The fenestrations 4 are arranged in a radiating pattern that extends outwardly away from the central point 6.

FIG. 1 shows two cardinal axes A-A and B-B and two intercardinal axes C-C and D-D, all intersecting at the central point 6. The pattern of fenestrations 4 contains fenestrations 10 having symmetry at least about cardinal axes A-A and B-B and fenestrations 11 having symmetry at least about intercardinal axes C-C and D-D. The pattern of fenestrations 4 further includes eight fenestrations 12 that are located in the secondary intercardinal regions. A fenestration 12 in one secondary intercardinal region has symmetry with another fenestration 12 in another secondary intercardinal region at least about the cardinal and intercardinal axes A-A, B-B, C-C and D-D.

The absorbent pad 3 has a laminate structure, in this embodiment comprising two layers 13, 14. The wound facing layer 13 is formed from a polyurethane foam and the second layer 14 is formed from a superabsorbent material.

The backing layer 2 has a border portion 16 that extends beyond the edges of the absorbent pad 3. The wound facing surface 17 of the border portion 16 is coated with an adhesive (not shown) to facilitate the adhesion of the wound dressing 1 to the wound-surrounding skin of a patient (not shown).

The backing layer 2 has a removable protecting layer 15 adhered to the distal surface of the backing layer 2. The removable protecting layer 15 comprises two removable parts 18, 19 which can be peeled off through pulling the tabs 20, 21.

In use, when a human or animal suffers a penetrating wound, the removable protecting layer 15 is removed from the wound dressing 1. The wound dressing 1 is then applied to the wound, with the wound facing surface 9 of the absorbent pad 3 being placed in direct contact with the wound. Upon application to a wound, the pattern of fenestrations 4 enables the absorbent pad 3 to stretch and readily conform to the contours of the anatomical area to which the wound dressing 1 is being applied. Once in place, force can be applied to the wound dressing 1 as necessary.

Figure 4:
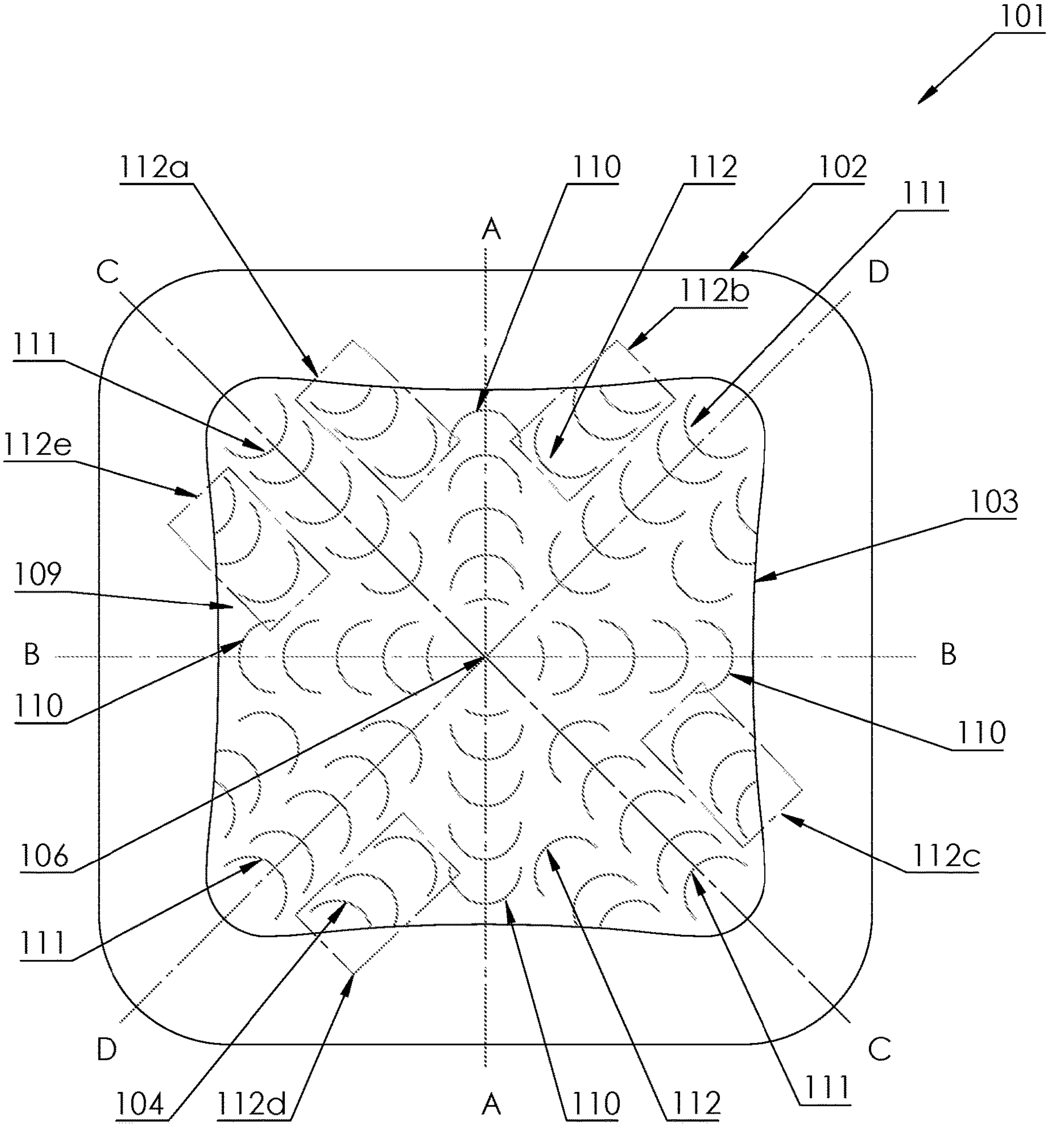
FIG. 4 is a plan view of a second embodiment of a wound dressing comprising an absorbent pad.

Turning to FIG. 4, there is shown an alternative pattern of fenestrations 104 in an absorbent pad 103. In this embodiment, the absorbent pad 103 comprises a plurality of fenestrations 104. Each of the fenestrations 104 has an arc shape. The majority of the fenestrations 104 have a semi-circular arc shape.

The absorbent pad 103 is in the shape of a rounded-edge square and has a wound facing surface 109 into which the fenestrations 104 are cut. The fenestrations 104 are arranged in a radiating pattern that extends outwardly from the central point 106.

In this embodiment, there is not a central fenestration located at a central point 106. Fenestrations 110 are located along the cardinal axes A-A and B-B and have symmetry at least about the cardinal axes A-A and B -B. The fenestrations 110 face away from the central point 106. Fenestrations 111 are located along the intercardinal axes C-C and D-D and have symmetry at least about the intercardinal axes C-C and D-D. Fenestrations 111 all face towards the central point 106. The pattern of fenestrations 104 further includes a plurality of fenestrations 112 located in the secondary intercardinal regions, wherein fenestrations in one secondary intercardinal region may have symmetry with fenestrations located in another secondary intercardinal region. For example, fenestrations 112*a* located in one secondary intercardinal region have symmetry with fenestrations 112*b*, 112*c*, 112*d*, 112*e* located in other secondary intercardinal regions at least about the cardinal and intercardinal axes A-A, B-B, C-C and D-D.

Figure 5:
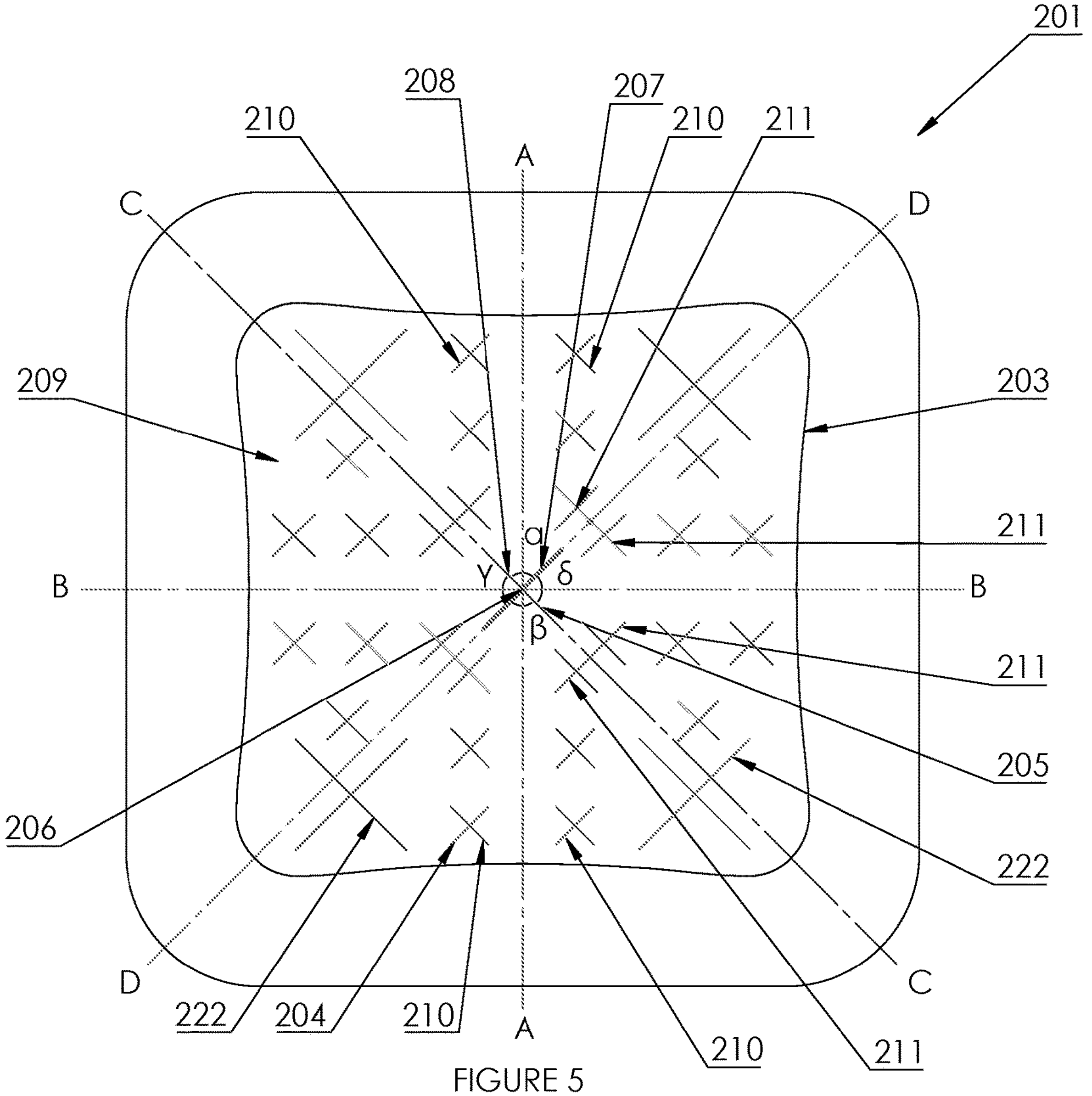
FIG. 5 is a plan view of a third embodiment of a wound dressing comprising an absorbent pad.

Turning to FIG. 5, there is shown an alternative pattern of fenestrations 204 in an absorbent pad 203. In this embodiment, the absorbent pad 203 comprises a plurality of fenestrations 204. Each of the fenestrations 204 has a cross shape. The cross shape is formed from a pair of slits intersecting at the midpoint of each slit, wherein each of the pairs of opposite angles add to 180°.

The absorbent pad 203 is in the shape of a rounded-edge square and has a wound facing surface 209 into which the fenestrations 204 are cut. The fenestrations 204 are arranged in a radiating pattern that extends outwardly from the central point 206.

A central fenestration 205 is located at a central point 206. The central fenestration 205 has a cross-shape, having two intersecting slits 207, 208. The intersecting slits 207, 208 create two pairs of opposite angles α, β and γ, δ. Each pair of opposite angles adds to 180°.

In this embodiment, there are no fenestrations located along the cardinal axes A-A and B-B. Fenestrations 210 are located within secondary intercardinal regions and have symmetry at least about the cardinal axes A-A and B-B. Fenestrations 211 are also located within secondary intercardinal regions and have symmetry at least about the intercardinal axes C-C and D-D. The pattern of fenestrations 204 further contains fenestrations 222 which are the substantially equivalent in size to the central fenestration 205. The fenestrations 222 are located in the corners of the absorbent pad 203.

Figure 6:
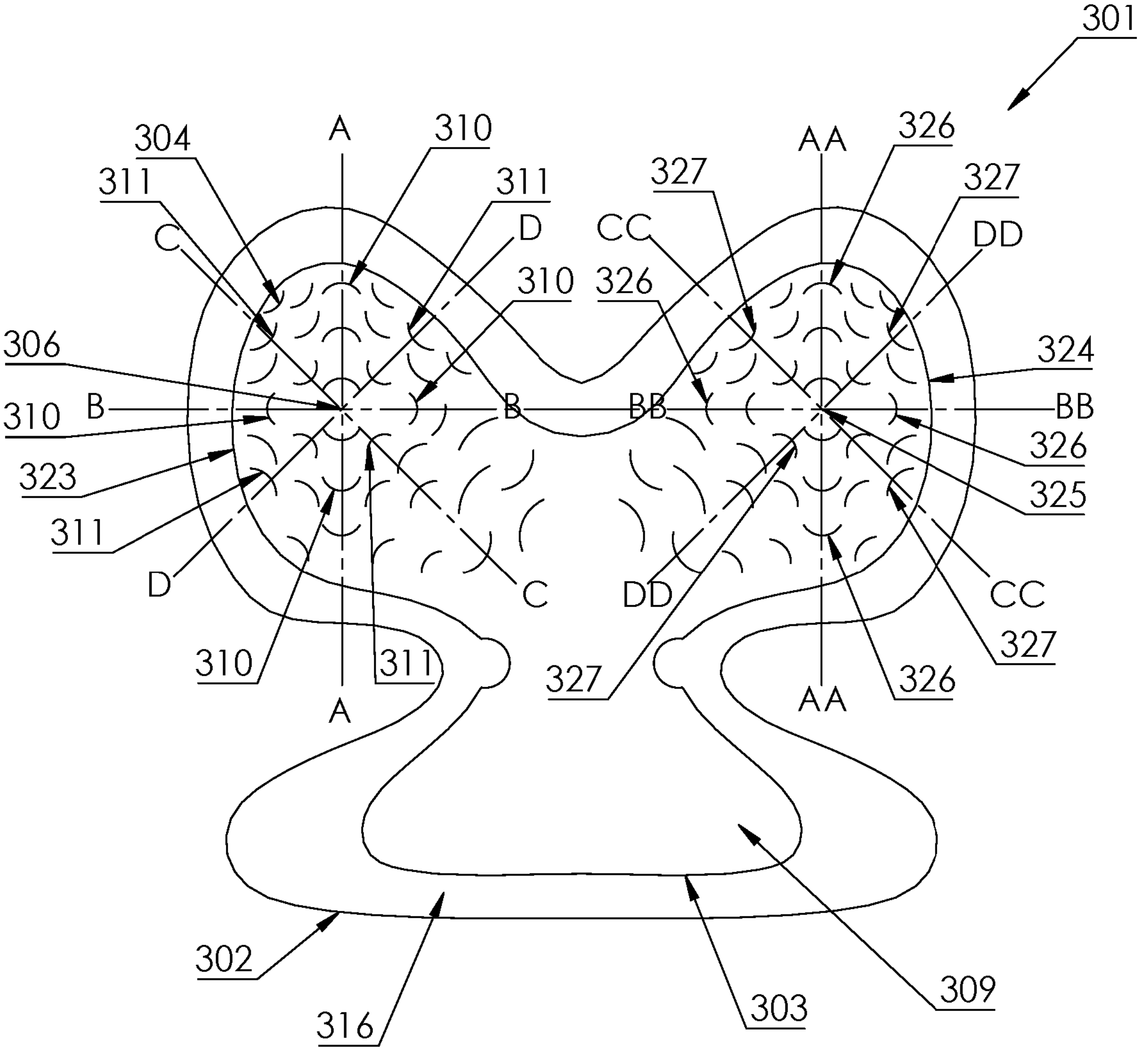
FIG. 6 is a plan view of a fourth embodiment of a wound dressing comprising an absorbent pad.

Turning to FIG. 6, there is shown a plan view of a wound dressing 301 that is shaped for use on the heel and ankle of a patient. The wound dressing 301 has a trilobal shape. The wound dressing 301 comprises a trilobal shaped backing layer 302 and an absorbent pad 303. The absorbent pad 303 is shaped to substantially follow the contours of the trilobal backing layer 302.

The backing layer 302 has a border portion 316 that extends beyond the edges of the absorbent pad 303. The wound facing surface 317 of the border portion 316 is coated with an adhesive (not shown) to facilitate the adhesion of the wound dressing 301 to the wound-surrounding skin of a patient (not shown).

The absorbent pad 303 comprises a plurality of fenestrations 304. The fenestrations are located in two of the lobes 323, 324 of the absorbent pad 303. Each of the fenestrations 304 has an arc shape. The majority of the fenestrations 304 have a shallow arc shape.

The absorbent pad 303 has a wound facing surface 309 into which the fenestrations 304 are cut. The fenestrations 304 within each lobe 323, 324 are arranged in a radiating pattern that extends outwardly from the central points 306, 325.

In this embodiment, there is not a central fenestration located at either central point 306, 325. Fenestrations 310 are located along the cardinal axes A-A and B-B and have symmetry at least about the cardinal axes A-A and B-B. The fenestrations 310 face away from the central point 306. Fenestrations 311 are located along the intercardinal axes C-C and D-D and have symmetry at least about the intercardinal axes C-C and D-D. Fenestrations 311 all face towards the central point 306. Correspondingly, Fenestrations 326 are located along the cardinal axes AA-AA and BB-BB and have symmetry at least about the cardinal axes AA-AA and BB-BB. The fenestrations 326 face away from the central point 325. Fenestrations 327 are located along the intercardinal axes CC-CC and DD-DD and have symmetry at least about the intercardinal axes CC-CC and DD-DD. Fenestrations 327 all face towards the central point 325.

EXAMPLES

Figure 7:
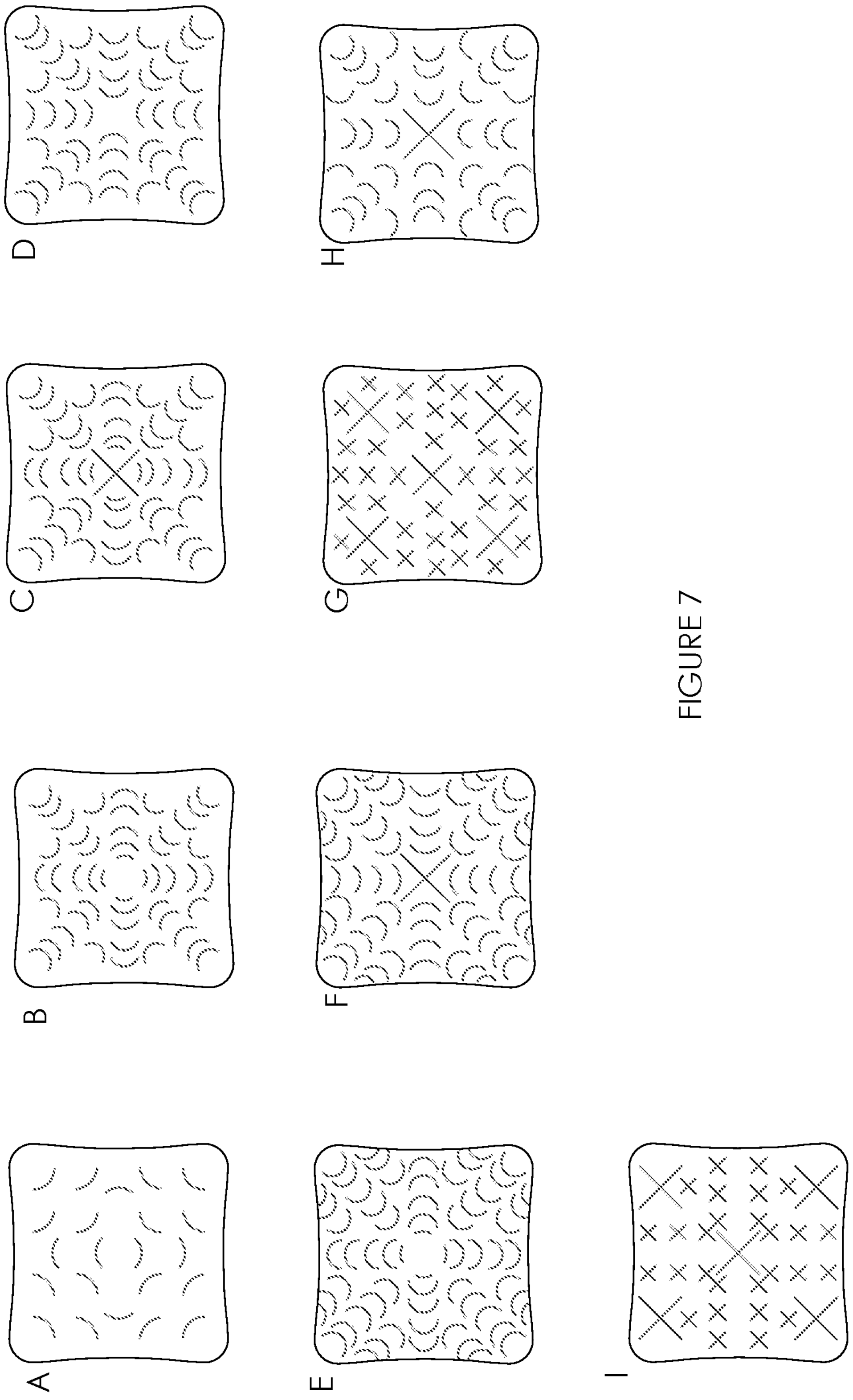
FIG. 7 is a plan view of nine different embodiments of fenestration patterns in an absorbent pad.

In order to evaluate the extensibility of absorbent pads according to the present invention, nine different fenestration patterns were tested according to the test method set out below. The nine different fenestration patterns are shown in FIG. 7. The nine fenestration patterns were tested against an absorbent pad having no fenestration pattern as a control.

Each of the test articles comprised a polyurethane backing film, an absorbent pad having the fenestration pattern cut therein and a perforated wound contact layer. The absorbent pad was adhered to the backing film using an acrylic adhesive. The acrylic adhesive was pattern coated onto the surface of the backing film. The absorbent pad was adhered to the wound contact layer using a silicone adhesive.

The absorbent pad formed a central island, comprising a superabsorbent air-laid material laminated with a polyurethane foam. The central island had a thickness of approximately 3-4.5 mm.

The extensibility and conformability test assess the extensibility and permanent set conformability of an absorbent pad.

Test Method (1) Cut out a 25 mm (±0.5) wide specimen for the sample material;

(2) After removing the specimen from the roll or backing film, allow it to relax for a minimum of 300 seconds (3) Place two parallel marks on the specimen 100 mm (±10) apart, such that the marks are at equal distance from the two ends. Measure the distance between the two marks to the nearest 0.5 mm (L1) using a calibrated ruler;

(4) Clamp the specimen outside the marks into the jaws of a tensile testing machine and extend the specimen by 20% using an extension rate of 300 mm/min (±10). Record the maximum load (ML) to the nearest 0.1N;

(5) Hold the specimen at this extension for 60 seconds (±1) then remove the specimen from the jaws and allow it to relax for 300 seconds (±15);

(6) Re-measure the distance between the two marks on the specimen (L2) using a calibrated ruler.

The extensibility of each sample was calculated using the formula:

$$\text{Extensibility } (\text{N}\cdot\text{cm}^{1}) = \text{ML}/2.5$$

The results of the extensibility testing for the absorbent pads is displayed in Table 1.

| | Extensibility (N/cm) | |
|---|---|---|
| | Pad | Wound dressing |
| Control | 7.58 | 3.16 |
| A | 4.49 | 2.97 |
| B | 2.41 | 2.93 |
| C | 2.24 | 2.95 |
| D | 2.81 | 3.06 |
| E | 2.32 | 2.97 |
| F | 1.97 | 2.71 |
| G | 2.27 | 2.81 |
| H | 3.03 | 2.85 |
| I | 2.95 | 2.86 |

Figure 8:
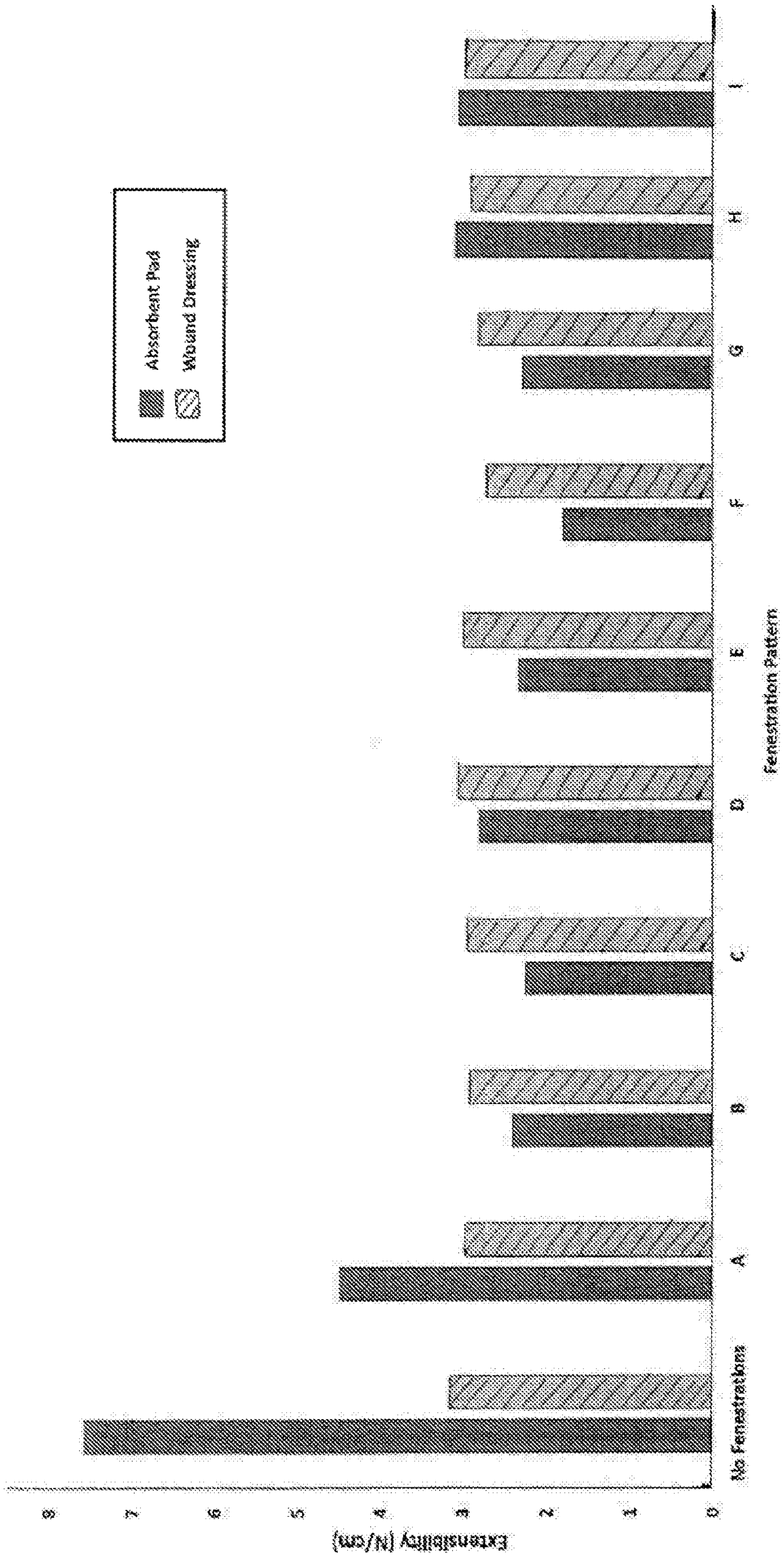
FIG. 8 is a graphical representation showing the extensibility of the nine embodiments shown in FIG. 7 and a control sample.

All of the tested samples A-I showed significantly increased extensibility over the control in both the absorbent pad and the wound dressing comprising the absorbent pad. The results in Table 1 have been graphed and can be seen in FIG. 8. The graph shows the significant improvement in extensibility of the Samples A-I of the present invention compared to the control sample having no fenestrations.

The various different fenestration patterns of Samples A-I were developed to better understand the contribution of design aspects such as increasing number of fenestrations (e.g. Sample B vs Sample A), the inclusion of a central fenestration (Sample C), having the arc fenestrations all facing towards the central point (Sample D), having the fenestration pattern extend to the edge of the absorbent pad (Sample E), combining several of these aspects (Sample F) and changing the shape of the fenestrations (Sample G). Lastly, Samples H and I were developed based on the good results observed for Samples F and G, respectively.

The good results observed for Sample F indicate that increasing the number of fenestrations, extending the fenestrations to the edge of the absorbent pad and introducing a central fenestration are all important factors to improving the extensibility of the absorbent pad and subsequent wound dressing. Of particular note are the comparatively beneficial results obtained where the pattern of fenestrations comprises a central fenestration having a different shape to the fenestrations radiating outwardly from the central point, such as in Sample F. In combination, the aforementioned design elements provide the best stretch and conformability of the designs tested.

The one or more embodiments are described above by way of example only. Many variations are possible without departing from the scope of protection afforded by the appended claims.

The invention claimed is:

1. An absorbent pad for a wound dressing, the pad having a plurality of fenestrations therein, wherein the fenestrations are arranged in a pattern about a central point, wherein the pattern comprises a plurality of arc-shaped fenestrations located on and having symmetry about a cardinal axis and a plurality of arc-shaped fenestrations located on and having symmetry about an intercardinal axis, the cardinal and intercardinal axes crossing at the central point.

2. The absorbent pad as claimed in claim 1, further comprising a central fenestration located at the central point.

3. The absorbent pad as claimed claim 2, wherein the fenestrations comprise slits; the pad comprises a central fenestration located at the central point; and wherein the fenestrations are present in two or more different geometrical shapes and/or two or more different sizes.

4. The absorbent pad as claimed in claim 2, wherein the central fenestration has rotational symmetry.

5. The absorbent pad as claimed in claim 2, wherein the central fenestration has n-fold rotational symmetry, wherein n is an integer from 2 to 10.

6. The absorbent pad as claimed in claim 2, wherein the central fenestration has the same shape as the fenestrations arranged about the central point.

7. The absorbent pad as claimed in claim 2, wherein the central fenestration has a different shape to the fenestrations arranged about the central point.

8. The absorbent pad as claimed in claim 2, wherein the central fenestration is larger than the fenestrations arranged about the central point.

9. The absorbent pad as claimed in claim 2, wherein the central fenestration has a triskelion shape or a tetraskelion shape.

10. The absorbent pad as claimed in claim 2, wherein the central fenestration has a cross shape comprising two intersecting slits or comprises two opposing arcs.

11. The absorbent pad as claimed in claim 1, wherein the pattern comprises a plurality of fenestrations having symmetry about one or more secondary intercardinal axes; or wherein the pattern comprises one or more fenestrations in one or more secondary intercardinal regions.

12. The absorbent pad as claimed in claim 11, wherein the pattern of fenestrations is symmetrical about at least one of the cardinal, intercardinal or secondary intercardinal axes.

13. The absorbent pad as claimed in claim 12, wherein the pattern of fenestrations is symmetrical about the cardinal axes and the intercardinal axes.

14. The absorbent pad as claimed in claim 1, wherein the pattern of fenestrations is radiating outwardly from the central point.

15. The absorbent pad as claimed in claim 14, wherein the fenestrations radiate outwardly from the central point along the cardinal and intercardinal axes; and optionally wherein additional fenestrations are located within one or more secondary intercardinal regions.

16. The absorbent pad as claimed in claim 15, wherein fenestrations located on the cardinal and intercardinal axes in one direction from the central point and the fenestrations located on the same cardinal and intercardinal axes in the opposite direction are equal in number.

17. The absorbent pad as claimed in claim 1, having a laminate structure.

18. The absorbent pad as claimed in claim 17, wherein the laminate structure comprises two layers.

19. A wound dressing comprising an absorbent pad as claimed in claim 1.

20. A wound dressing as claimed in claim 19 for use in absorbing fluid discharged from a physiological target, or for use in stemming a flow of a fluid discharged from a physiological target site.

21. The absorbent pad as claimed in claim 1, wherein one or more of the fenestrations has an arc shape that faces towards the central point.

22. The absorbent pad as claimed in claim 1, wherein the fenestrations are present in two or more different geometrical shapes and/or two or more different sizes.

23. The absorbent pad as claimed in claim 1, wherein the pattern further comprises a plurality of arc-shaped fenestrations located on and having symmetry about another cardinal axis, wherein the cardinal axes are perpendicular to each other and intersect at the central point.

24. The absorbent pad as claimed in claim 1, wherein the pattern further comprises a plurality of arc-shaped fenestrations located on and having symmetry about another intercardinal axis, wherein the intercardinal axes are perpendicular to each other and intersect at the central point.

25. The absorbent pad as claimed in claim 1, wherein one or more fenestrations have a cross shape.

26. The absorbent pad as claimed in claim 1, wherein the fenestrations penetrate through the entire thickness of the absorbent pad; or wherein the fenestrations penetrate partially through the thickness of the absorbent pad.

27. An absorbent pad as claimed in claim 1 for use in absorbing fluid discharged from a physiological target, or for use in stemming a flow of a fluid discharged from a physiological target site.

28. A method of manufacturing an article, said method comprising applying a plurality of fenestrations to an absorbent pad, wherein the fenestrations are arranged in a pattern about a central point, wherein the pattern comprises a plurality of arc-shaped fenestrations located on and having symmetry about a cardinal axis and a plurality of arc-shaped fenestrations located on and having symmetry about an intercardinal axis, the cardinal and intercardinal axes crossing at the central point.

* * * * *